United States Patent
Wickham et al.

[19]

[11] Patent Number: 6,159,186
[45] Date of Patent: Dec. 12, 2000

[54] INFUSION DELIVERY SYSTEM

[75] Inventors: Terrence Wickham, Krugersdorp; Brian Clement Goemans, Randburg, both of South Africa

[73] Assignee: WFT Projects (Proprietary) Limited, Blairgowrie, South Africa

[21] Appl. No.: 09/267,454

[22] Filed: Mar. 12, 1999

[30] Foreign Application Priority Data

Mar. 13, 1998 [ZA] South Africa .......................... 98/2143

[51] Int. Cl.⁷ .................................................. A61M 5/00
[52] U.S. Cl. .......................... 604/251; 604/253; 604/65; 604/66
[58] Field of Search ................. 604/65, 66, 67, 604/30, 31, 251, 253

[56] References Cited

U.S. PATENT DOCUMENTS

| | | | |
|---|---|---|---|
| 4,328,801 | 5/1982 | Marx et al. | 128/214 |
| 4,936,828 | 6/1990 | Chiang | 604/65 |
| 5,186,057 | 2/1993 | Everhart | 73/861.41 |
| 5,331,309 | 7/1994 | Sakai | 340/606 |
| 5,588,963 | 12/1996 | Roelofs | 604/65 |
| 5,856,200 | 1/1999 | Krause et al. | 436/180 |

FOREIGN PATENT DOCUMENTS

0641599 A1  3/1995  European Pat. Off. .

OTHER PUBLICATIONS

Abstract of Japanese Patent No. JP 7,333,231, dated Dec. 22, 1995.

*Primary Examiner*—John D. Yasko
*Attorney, Agent, or Firm*—Jenkins & Gilchrist, P.C.

[57] ABSTRACT

Apparatus for providing control of infusion delivery using conventional infusion fluid bags includes an air bag which is pressurised by a pneumatic pump. A digital camera or imaging device is able to analyse drops passing through a drop chamber, by capturing an image of the drop as it passes through the drop chamber. The output of the imaging device is fed to an image processor which calculates the volume of the captured drop using the number of pixels in the image. An infra red detector detects each time a drops passes through the drop chamber, and the outputs of the both the image processor and the infra red detector are passed to a master controller. The master controller controls the fluid delivery process by counting the number of drops passing through the drop chamber and controlling a flow brake to achieve the required flow rate.

9 Claims, 10 Drawing Sheets

SYSTEM BLOCK DIAGRAM

PUMP OPERATION OVERVIEW

Fig 4

PUMP OPERATION

Fig 5

PROMPT LOAD / UNLOAD

Fig 6

INITIATE PUMPING

Fig 7

MAINTAIN PUMPING

Fig 8

TERMINATE PUMPING

Fig 9

ANALYSE IMAGE

Fig 10

CHECK STATUS

Fig 12 INTERIOR VIEW

Fig 11 EXTERNAL VIEW

INFUSION DELIVERY SYSTEM

BACKGROUND OF THE INVENTION

THIS invention relates to apparatus for controlling infusion delivery.

Medical infusion delivery systems are available which use peristaltic pumps and which generally require the use of specially designed intravenous (IV) administration sets. In order to reduce the cost of providing an infusion delivery system, it would be desirable to be able to use conventional IV sets. It would also be desirable to reduce the cost, particularly by doing away with the need for a peristaltic pump, or other volumetric displacement system, while maintaining or even improving the accuracy of the system.

It is an object of the invention to provide apparatus for controlling infusion delivery which can utilise conventional IV sets and which can provide high accuracy.

SUMMARY OF THE INVENTION

According to the invention there is provided apparatus for controlling infusion delivery via a drop chamber having an inlet for liquid, an outlet below the inlet, and a space between be inlet and the outlet, the apparatus comprising:

imaging means for recording data corresponding to images of drops falling through the drop chamber;

first processor means for calculating the volume of the drops from the recorded data and thus the liquid flow rate through the drop chamber; and control means for comparing the calculated liquid flow rate with a desired or predetermined flow rate value and for controlling the flow rate of liquid entering and/or leaving the drop chamber to correspond to the desired or predetermined value.

The imaging means preferably comprises a digital image sensor, such as a CCD or active pixel sensor device.

The imaging means preferably includes drop detection means for detecting each drop falling through the drop chamber, the first processor means being arranged to calculate the liquid flow rate through the drop chamber from the number of drops detected and the calculated volume of selected drops.

The drop detection means is preferably arranged to generate a trigger signal when a falling drop is detected, the trigger signal triggering a light source to illustrate the falling drop briefly for recordal of a "frozen" image thereof by the imaging means.

The control means preferably includes second processor means arranged to operate pump means for supplying liquid to the inlet of he drop chamber from a reservoir, and brake means arranged to control the flow of liquid downstream from the outlet of the drop chamber.

The apparatus may include a housing for receiving a flexible reservoir, typically an IV solution bag, the housing further including location means adapted to locate and support tide drop chamber adjacent the imaging means for correct operation thereof.

The pump means may comprise a pneumatic pump in the housing arranged to pressurise the reservoir, and pressure sensor means for providing a reservoir pressure signal to the second processor means.

The brake means may comprise a brake member operated by a solenoid or other actuator means arranged to constrict a conduit connected to the outlet of the drop chamber, thereby to restrict the flow of liquid in the conduit.

BRIEF DESCRIPTION OF THE DRAWINGS

The invention will now be described in more detail, by way of example only, with reference to the accompanying drawings in which.

DESCRIPTION OF A PREFERRED EMBODIMENT

The apparatus of the present invention was designed to provide accurate control of infusion delivery using conventional infusion fluid bags. The apparatus comprises an enclosure sized to receive a conventional IV solution bag or infusion bag 10, the bag being suspended upright within the enclosure. The enclosure has a front panel or door, with a pressurizing system comprising an air bag 12 which is pressurised by a pneumatic pump 14 to provide a driving pressure to the liquid in the bag 10 (see FIG. 1). One or more liquid level sensors 16 are mounted in the enclosure or on its door, to monitor the level of liquid in the bag 10. The bag pressurising system includes a pressure sensor 18 which provides an output pressure signal which is utilised as described below, as well as an over pressure switch 20 which provides an output signal when the pressure in the bag exceeds an upper threshold.

Figure 11:
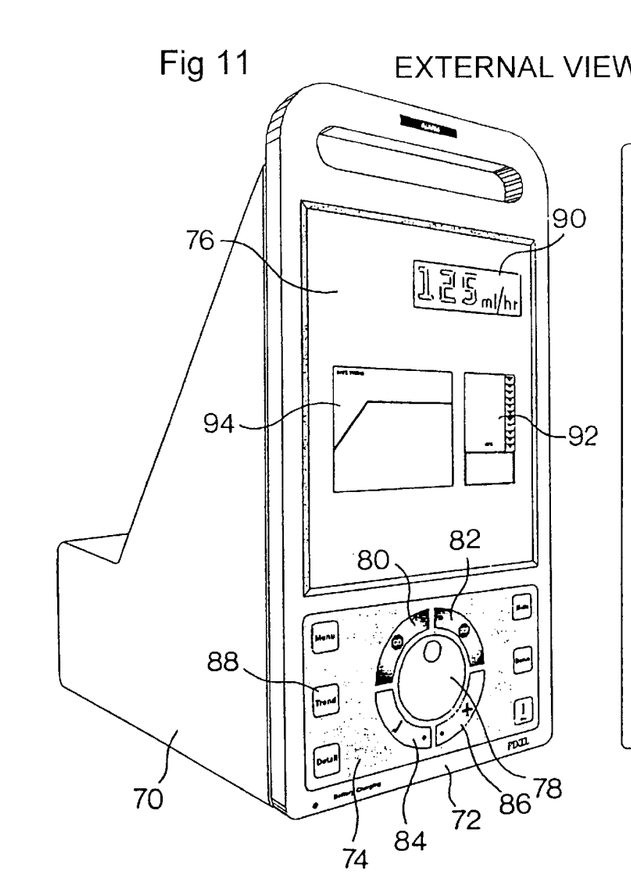
FIG. 11 is a pictorial view of a prototype of the control apparatus.

FIG. 11 is a pictorial view of a prototype of the apparatus. The apparatus comprises a compact housing 70 with a generally rectangular front panel 72 which is hinged to the front of the housing so tat it can be opened to permit insertion and removal of an infusion bag 10. On the front panel 72 are a control panel 74 and a display panel 76. The control panel comprises a central control wheel or dial 78 surrounded by four sector-shaped primary keys 80, 82, 84 and 86. These keys are designated GO, STOP, CONFIRM and CANCEL, respectively. Several secondary functions are accessed via six secondary keys 88, which included a MENU key and a HELP key.

The display panel 76 includes a numeric display 90 which provides a numeric read-out of the flow rate in ml/h of liquid being delivered by the apparatus. The display panel also includes a first graphic display 92 which indicates the level of liquid in the infusion bag 10 within the housing, and a second graphic display 94 which indicates the flow rate trend in a graphical form.

Figure 12:
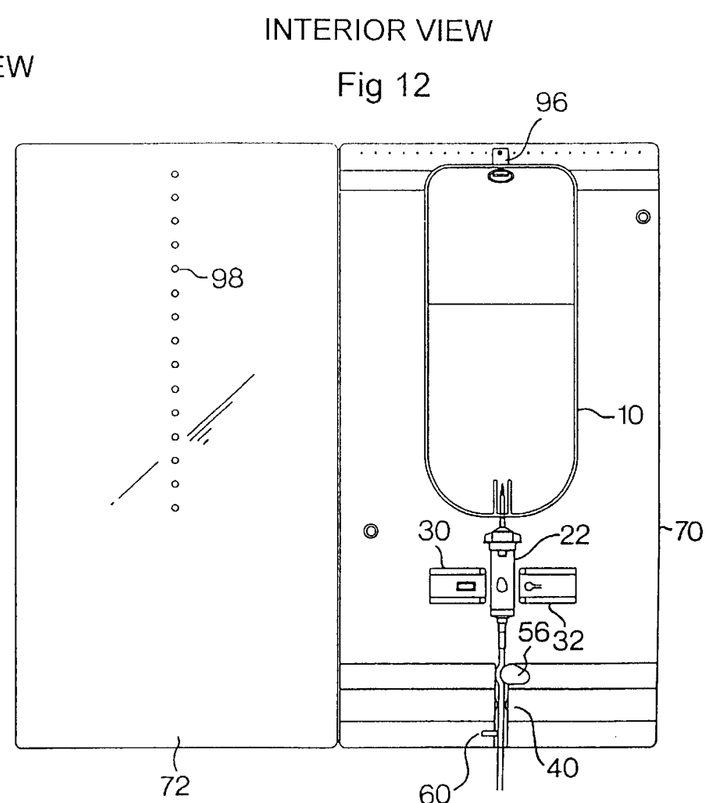
FIG. 12 is a front view of the apparatus with its front panel swung open to show its interior.

The interior of the apparatus is illustrated in FIG. 12. An adjustable hanger 96 is provided at the upper end of the housing, allowing the infusion bag 10 to be hung inside the enclosure and positioned correctly. Optical sensors 98 arranged in a row on the inside of the front panel 72 are in contact with the side of the bag 10 when the front panel is closed, and monitor the level of liquid in the bag.

The housing 70 includes a recess towards its lower end for locating a transparent cylindrical drop chamber 22, which is attached to the bag 10 conventionally by a spike, with a spring loaded clamp being provided to hold the drop chamber in position. In the rear of the enclosure door 72 is a white light source 24 arranged to illuminate the drop chamber momentarily from time to time. Also mounted in the enclosure, behind and adjacent to the drop chamber, is a digital camera or imaging device 28, a pair of infrared detectors 30 and 32, and an infrared light source 26. A mechanical interlock in the enclosure door ensures that the door is properly closed before the system is enabled.

The preferred digital camera or imaging device 28 is an active pixel sensor (APS) device which is essentially a "camera on a chip" which outputs a digital signal at a typical resolution of 256 by 256 pixels. With a 16 bit microprocessor implementing suitable image processing algorithms (see below) processing time is approximately 1 second, so that data can be clocked off the image sensor at a rate of approximately 1 frame per second. In the intended application, it is not necessary to analyse each drop passing through the drop chamber, but in other applications, a higher data throughput might be desirable. The APS technology allows random access readout from the image sensor, thus facilitating a simple electronic "zoom" or "pan" function, allowing the system to compensate for small variations in drop chamber positioning.

With a 256 by 256 pixel image sensor the measurement of drop size is subject to an error due to quantisation of approximately 2%, which is acceptable for the present purposes.

Figure 1:
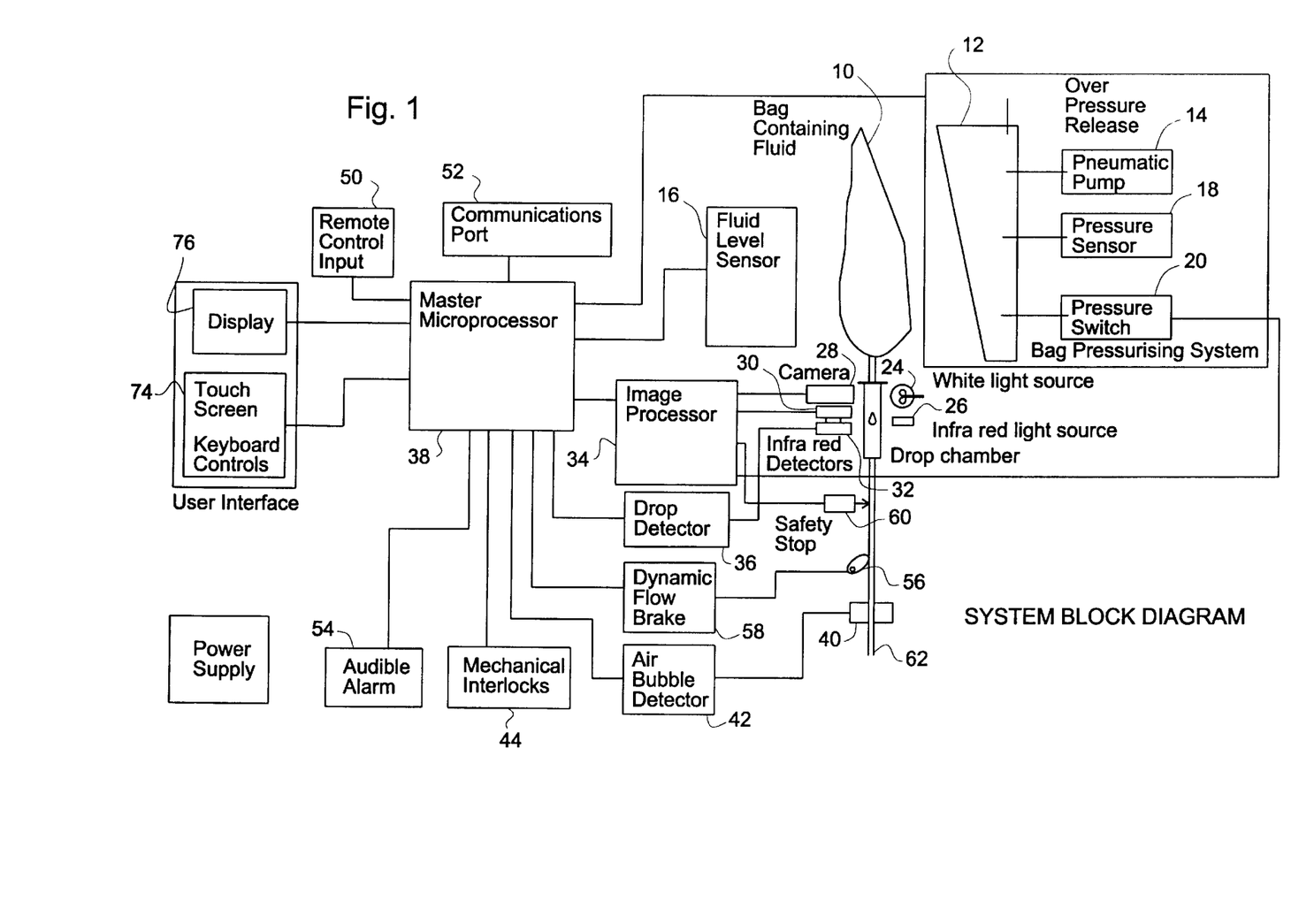
FIG. 1 is an overall block diagram of infusion delivery control apparatus according to the invention.

The output of the imaging device 28 and the output of the first infrared detector 30 are fed to an image processor 34, while the output of the second infrared detector 32 is fed to a drop detector circuit 36 which in turn provides an output to a master microprocessor 38.

The master microprocessor also receives inputs from all ultrasonic air bubble detector sensor 40 via an air bubble detector circuit 42 and from the mechanical interlocks 44 associated with the enclosure 70 and the door of the front panel 72. In addition, the master microprocessor controls the fluid delivery process, controlling the pneumatic pump 14 and receiving pressure signals from the pressure sensor 18. The display panel 76 and the control panel 74 provide the necessary user interface for operation of the apparatus. The master microprocessor 38 also accepts a remote control input 50 and has a communications port 52 for transmission of data to other processing devices, a printer or the like. Outputs from the master microprocessor control an audible alarm 54 and a dynamic flow brake 56 via a dynamic flow brake circuit 58.

The master microprocessor 38 controls the fluid delivery process, by counting the number of drops passing through the drop chamber 22 and controlling the flow brake 56 to achieve Me required flow rate. The image processor 34 computes the volume of the drops, within defined drop rate norms, and also performs a checking function to enhance the safety of the system, receiving an output from the over pressure switch 20 and controlling a solenoid safety stop 60.

When pumping commences, the master processor informs the image processor of the expected drop rate (corresponding to a predetermined value or a value set by a user of the apparatus). Using the output of the infrared detector 30 as a trigger, the image processor 34 commences its image capture routine.

On receipt of the trigger signal from the infrared detector 30, the CCD imaging device 28 is prepared for image capture. The image processor then briefly illuminates or strobes he white light source 24, illuminating the falling drop for a very short period of time, effectively "freezing" it in free fall. Once the drop image has been strobed onto the imaging device, it may be read off at any convenient rate irrespective of the further passage of drops in the drop chamber, as the view field is held in darkness.

While a captured image is being processed, any fiber drops that fall are counted. Once the volume of the captured drop has been computed, the volume value is reported to the master micro processor, and the image microprocessor captures an image of the next falling drop. If the image microprocessor detects that drops are falling too rapidly, this is reported to the master microprocessor. If the problem is not rectified within a given period, the image microprocessor can stop the flow completely by activating the safety stop 60.

Another potential runaway fault which the image processor will prevent is over pressurisation of the bag 10 by the pressurising system 12. The master microprocessor 38 turns the pneumatic pump on and off to keep the pressure within he air bag 12 of the pneumatic pump within a predetermined range. The pressure switch 20 closes at a predetermined pressure and informs the image microprocessor that the pressure in the air bag 12 is out of limits, allowing the image microprocessor to activate the safety stop, which is also activated in the event of a power supply fault.

Because the two microprocessors of the apparatus are communicating continuously, they can monitor each other to detect an error condition. In this case, the image processor can operate the safety stop, or the master microprocessor can operate the flow brake.

Figure 2:
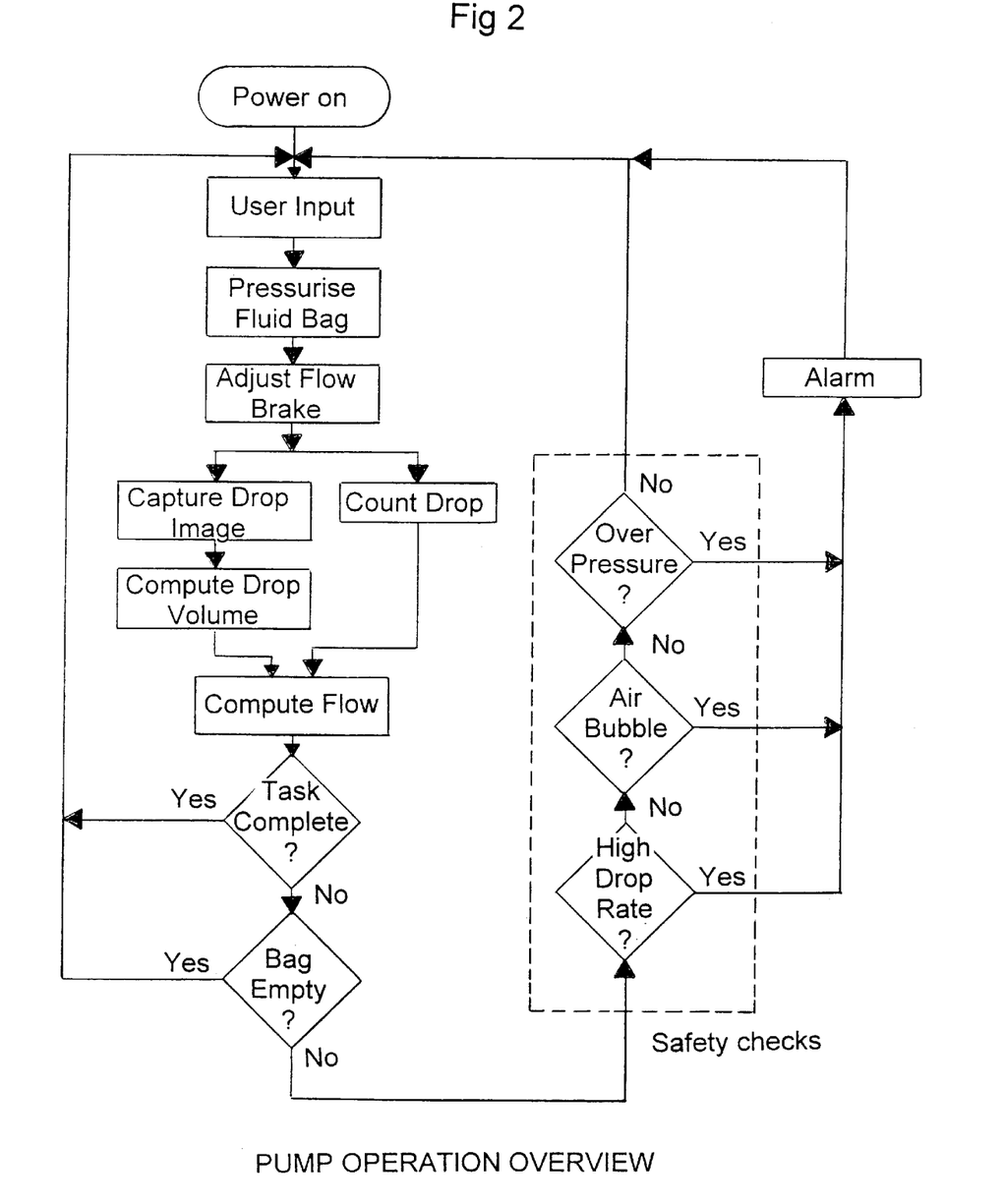
FIGS. 2 to 10 are flow charts illustrating the operation of the apparatus.

The bubble detector 40 monitors the IV line 62 for air bubbles, and provides a signal to the master microprocessor 38 via the detector circuit 42, allowing an alarm to be generated if air bubbles are detected. The master microprocessor 38 can also detect an occlusion of the IV Line 62, by detecting an absence of drops falling despite the application of pressure to the bag 10 via the pressurising system 12. The above procedure is summarised in the flow chart of FIG. 2.

Depending on the user configuration of the apparatus, the apparatus may stop an infusion when a required volume has been delivered, requesting additional user input for further action. If the bag 12 is emptied, the infusion is also halted. The detection of a fault will either stop the pump or reduce the liquid flow to a minimum to maintain the fluid pathway to the patient (known as KVO rate).

Figure 3:
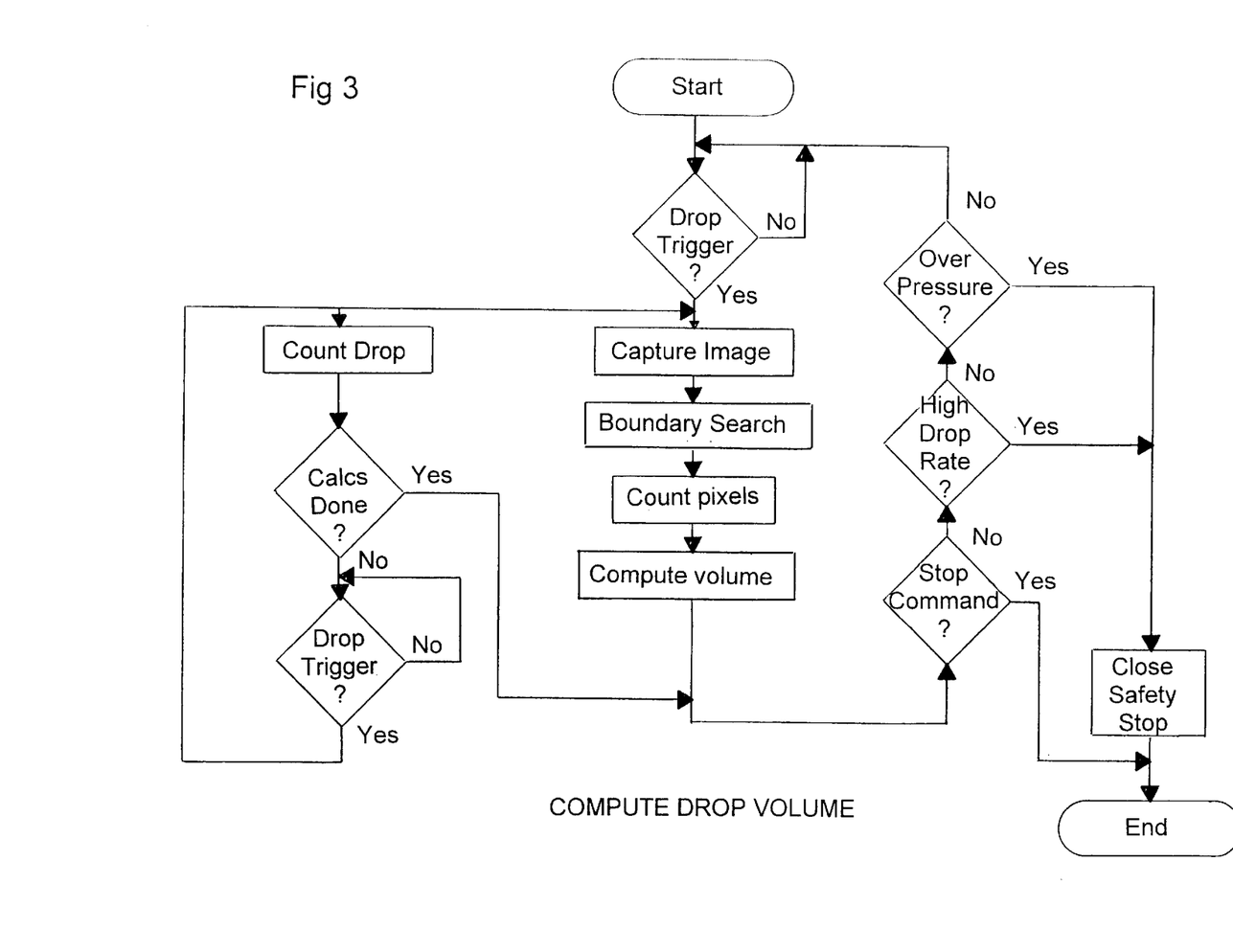

The flow chart of FIG. 3 summarises the image processing algorithms which are implemented by the me microprocessor 34 to determine the volume of captured drops. Once the drop image has been captured, its boundary is identified by a boundary tracking algorithm. The pixels within this boundary are counted, and the image is then rotated in the vertical plane to derive the volume of the drop. The drop is assumed to be symmetrical about its vertical axis.

Figure 4:
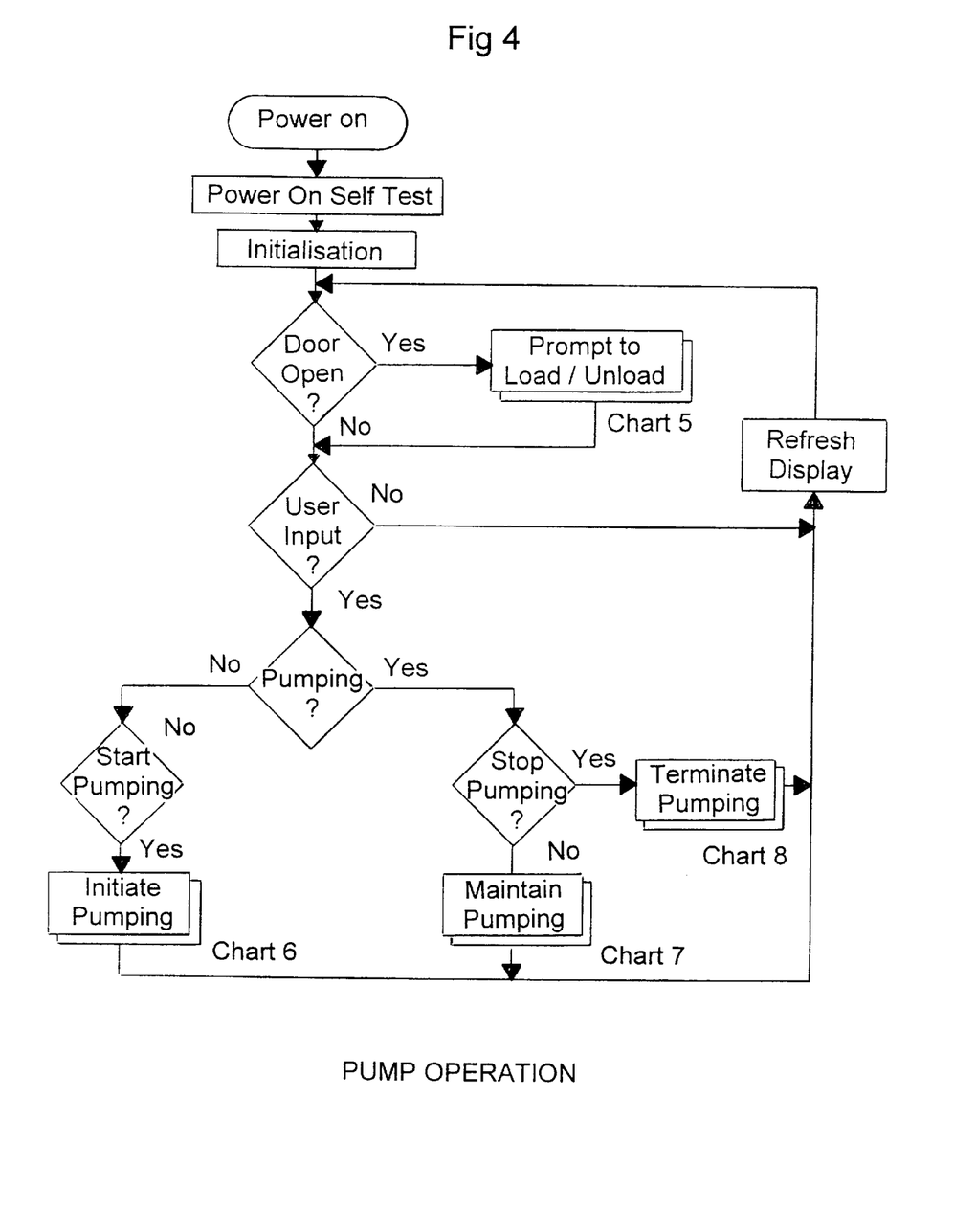
Figure 5:
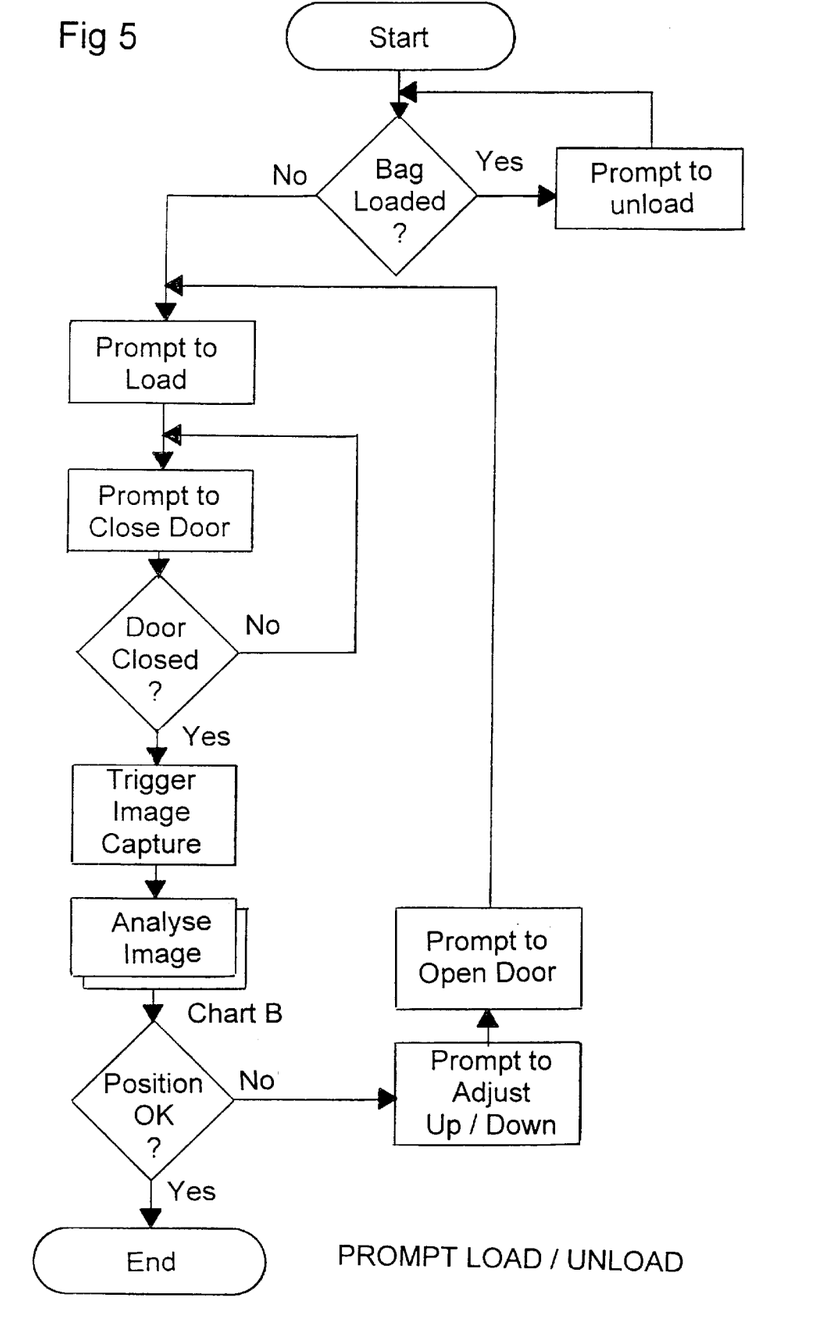

The flow chart of FIG. 4 summarises the user interface functions of the apparatus, with reference to the associated flow charts herein. The flow chart of FIG. 5 summarises the bag positioning procedure in the enclosure. It is important that the position of the drop amber be within certain limits for correct operation of the image sensor. Once the bag has been loaded and the door of the enclosure closed, an image of the drop chamber is captured and analysed, and the user is prompted to adjust the position of the drop chamber if it is not in the correct position.

Figure 6:
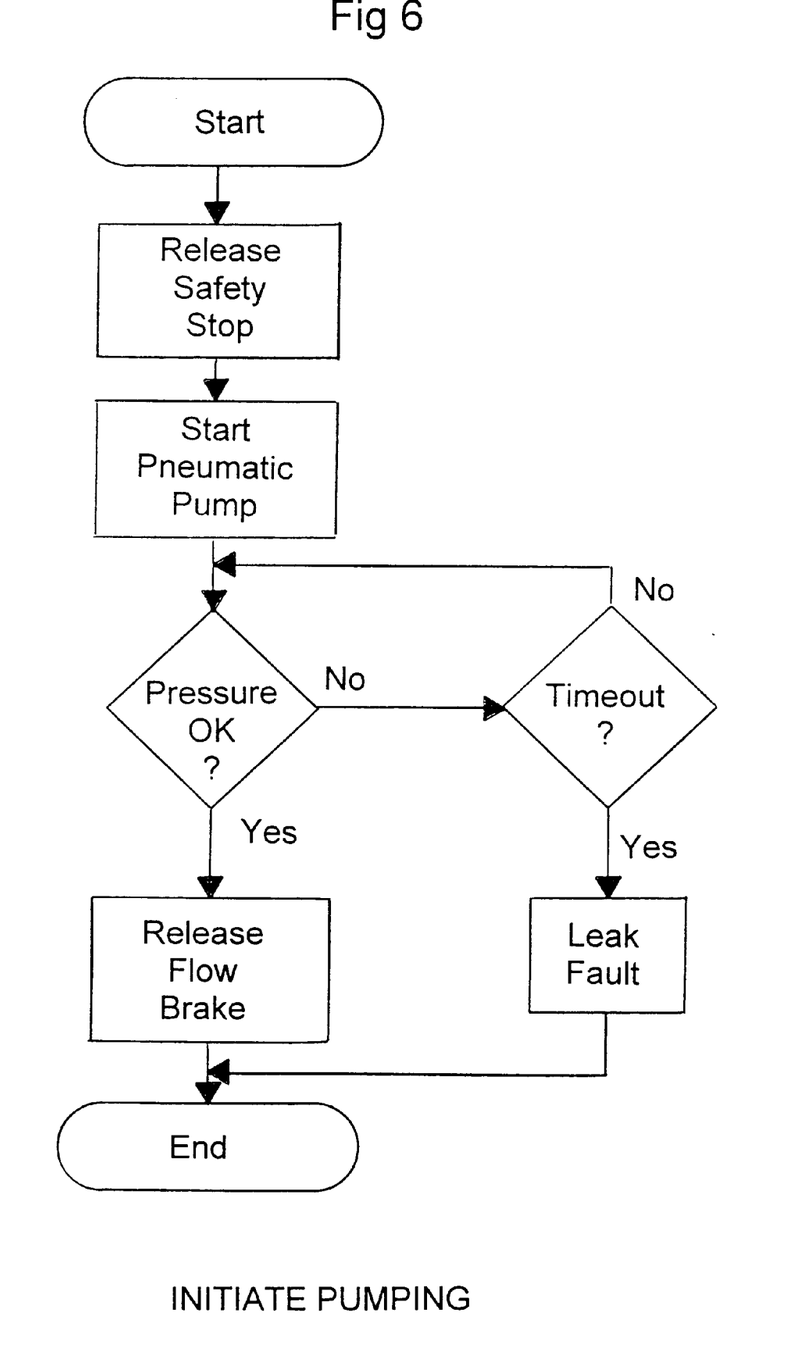
Figure 7:
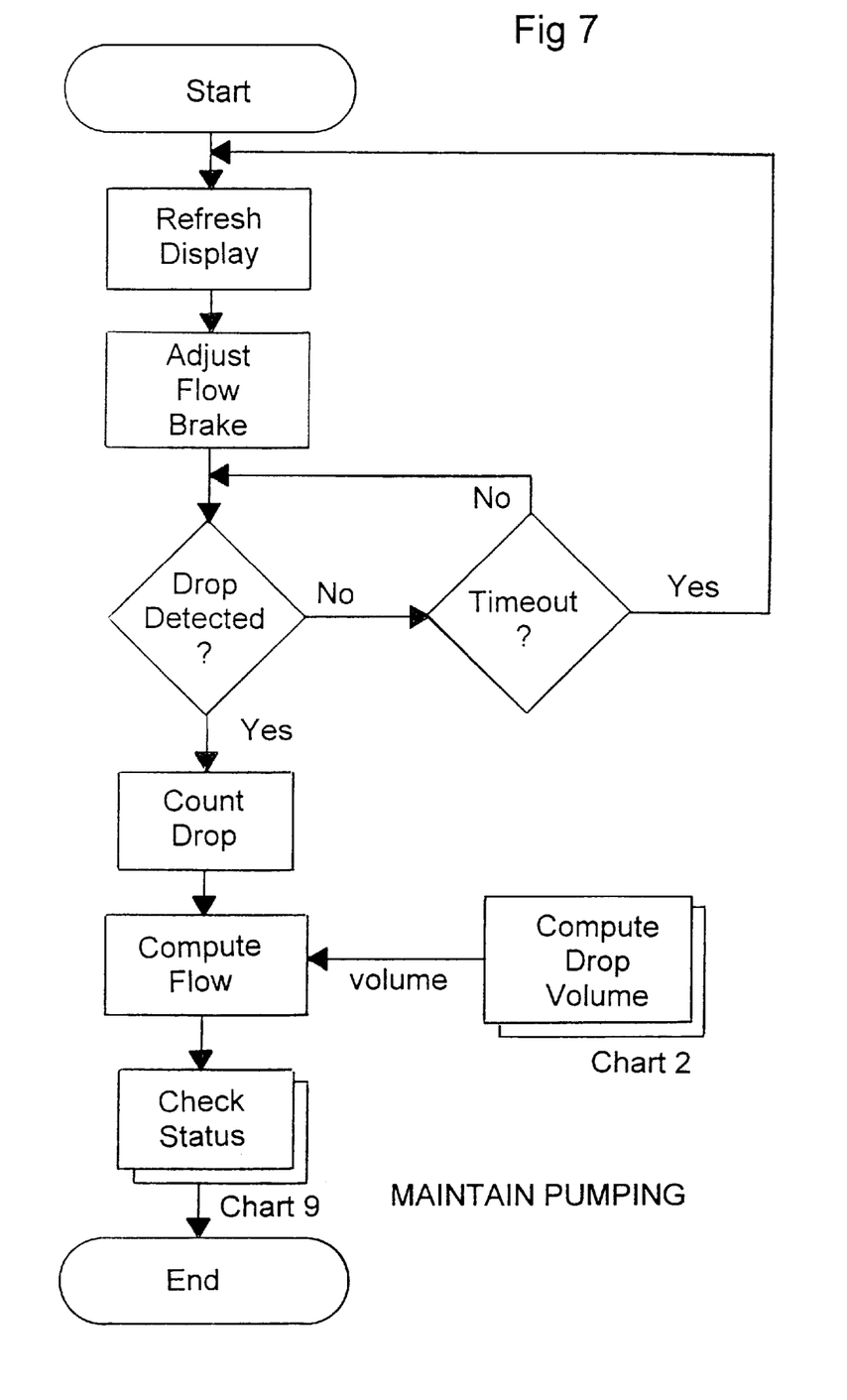
Figure 8:
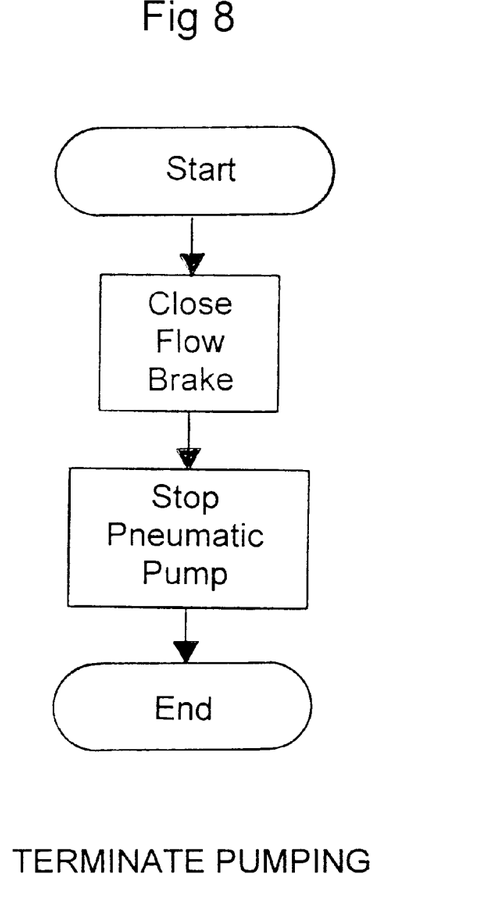
Figure 9:
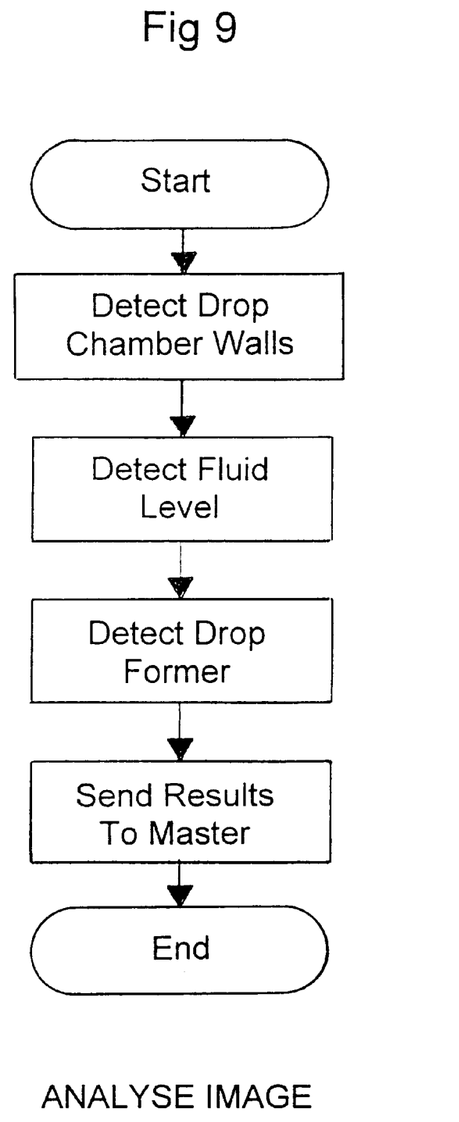
Figure 10:
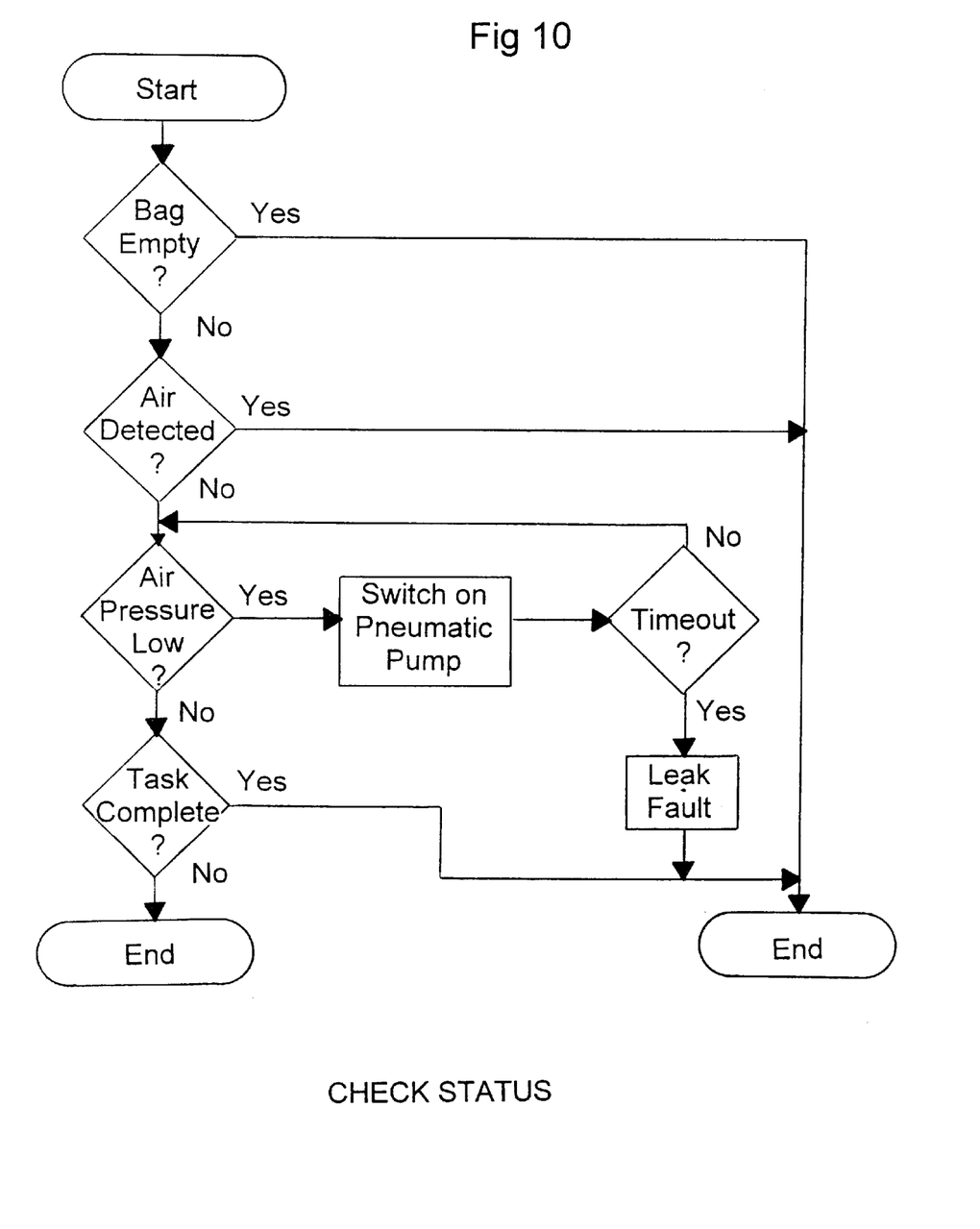

The flow charts of FIGS. 6 and 7 illustrate the procedures followed by the apparatus in commencing and maintaining pumping, while the flow chart of FIG. 8 reflects the termination of pumping. The flow chart of FIG. 9 shows a sub-routine (which is referred to in the flow chart of FIG. 5) relating to the drop chamber location process. An image of the drop chamber is analysed to verify its position, with the drop chamber walls being identified as vertical lines, the fluid levels as a horizontal line, and the drop former as a protrusion into the drop chamber from above. The position of the chamber relative to location markings is also monitored.

The described apparatus can provide a highly linear and accurate flow at the lowest infusion pressure necessary, and with highly accurate calculation of the volume of liquid delivered. This is achieved at low cost, due to the absence of complex mechanical components. The use of a sophisticated active pixel sensor imaging device allows drop volume calculation to be performed by a microprocessor, rather tan relying on volumetric displacement as in the case of typical peristaltic or piston-type pumps.

We claim:

1. Apparatus for controlling infusion delivery via a drop chamber having an inlet for liquid, an outlet below the inlet, and a space between the inlet and the outlet, the apparatus comprising:

drop detection means for detecting each drop of a plurality of drops falling through the chamber and for providing a trigger signal on detection thereof;

a light source ressponsive to the trigger signal to illuminate falling drops briefly for recordal of a frozen image thereof;

imaging means defining a two-dimensional multi-pixel array for acquiring data corresponding to two-dimensional images of drops falling through the drop chamber;

first processor means for calculating the volume of the drops from the data by calculating the number of pixels in each drop image, and for calculating the liquid flow rate through the drop chamber from the calculated volume of the imaged drops and the number of drops detected; and control means for comparing the calculated liquid flow rate with a desired or predetermined flow rate value and for controlling the flow rate of liquid entering and/or leaving the drop chamber to correspond to the desired or predetermined value.

2. Apparatus according to claim 1 wherein the imaging means is a CCD or active pixel sensor device.

3. Apparatus according to claim 1 wherein the first processor means is arranged to calculate the liquid flow rate through the drop chamber from the number of drops detected and the calculated volume of selected drops, the number of selected drops being smaller than the total number of drops.

4. Apparatus according to claim 1 wherein the control means includes second processor means arranged to operate pump means for supplying liquid to the inlet of the drop chamber from a reservoir, and brake means arranged to control the flow of liquid downstream from the outlet of the drop chamber.

5. Apparatus according to claim 4 wherein the apparatus includes a housing for receiving a flexible reservoir containing liquid which is delivered via an associated drop chamber in use, the housing further including location means adapted to locate and support the drop chamber adjacent the imaging means for correct operation thereof.

6. Apparatus according to claim 5 wherein the first processor means is arranged to receive data from the imaging means corresponding to the position of the drop chamber relative to the location means and to carry out a drop chamber location routine by comparing the received data with reference position data, thereby to ensure correct location of the drop chamber relative to the imaging means in use.

7. Apparatus according to claim 5 wherein the flexible reservoir is an IV solution bag.

8. Apparatus according to claim 5 wherein the pump means comprises a pneumatic pump in the housing arranged to pressurize the reservoir, and pressure sensor means for providing a reservoir pressure signal to the second processor means.

9. Apparatus according to claim 1 wherein the brake means comprises a brake member operated by a solenoid or other actuator means arranged to constrict a conduit connected to the outlet of the drop chamber, thereby to restrict the flow of liquid in the conduit.

* * * * *

UNITED STATES PATENT AND TRADEMARK OFFICE
CERTIFICATE OF CORRECTION

PATENT NO.   : 6,159,186
DATED        : December 12, 2000
INVENTOR(S)  : Terrence Wickham et al.

It is certified that error appears in the above-identified patent and that said Letters Patent is hereby corrected as shown below:

Title page,
Attorney, Agent, or Firm, replace "Jenkins" with -- Jenkens --

Column 1,
Line 47, replace "he" with -- the --
Line 53, replace "tide" with -- the --

Column 2,
Line 31, replace "tat" with -- that --

Column 3,
Line 42, replace "Me" with -- the --
Line 56, replace "he" with -- the --
Line 63, replace "fiber" with -- further --

Column 4,
Line 9, replace "he" with -- the --
Line 24, replace "Line" with -- line --
Line 37, replace "me" with -- image --
Line 48, replace "amber" with -- chamber --

Column 5,
Line 5, replace "tan" with -- than --

Signed and Sealed this

Fifth Day of March, 2002

Attest:

JAMES E. ROGAN
Attesting Officer / Director of the United States Patent and Trademark Office